(12) United States Patent
Zeng et al.

(10) Patent No.: US 9,540,686 B2
(45) Date of Patent: Jan. 10, 2017

(54) SYSTEMS AND METHODS FOR THE AMPLIFICATION OF DNA

(75) Inventors: Shulin Zeng, Gaithersburg, MD (US); Kenton C. Hasson, Gaithersburg, MD (US); Gregory A. Dale, Gaithersburg, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 493 days.

(21) Appl. No.: 12/233,194

(22) Filed: Sep. 18, 2008

(65) Prior Publication Data

US 2010/0068765 A1    Mar. 18, 2010

(51) Int. Cl.
*C12Q 1/68* (2006.01)
*B01L 3/00* (2006.01)
*B01L 7/00* (2006.01)

(52) U.S. Cl.
CPC ......... *C12Q 1/686* (2013.01); *B01L 3/502715* (2013.01); *B01L 7/525* (2013.01); *B01L 2200/147* (2013.01); *B01L 2300/0816* (2013.01); *B01L 2300/0883* (2013.01); *B01L 2300/1822* (2013.01); *B01L 2300/1827* (2013.01); *B01L 2300/1838* (2013.01); *B01L 2400/0487* (2013.01)

(58) Field of Classification Search
CPC ............... B01L 2300/1838; B01L 2300/185
See application file for complete search history.

(56) References Cited

U.S. PATENT DOCUMENTS

| | | | |
|---|---|---|---|
| 5,508,197 A | 4/1996 | Hansen et al. | |
| 5,720,923 A * | 2/1998 | Haff et al. | 422/68.1 |
| 5,871,908 A | 2/1999 | Henco et al. | |
| 6,140,054 A | 10/2000 | Wittwer et al. | |
| 6,171,850 B1 | 1/2001 | Nagle et al. | |
| 6,174,670 B1 | 1/2001 | Wittwer et al. | |
| 6,413,766 B2 | 7/2002 | Landers et al. | |
| 6,472,156 B1 | 10/2002 | Wittwer et al. | |
| 6,569,627 B2 | 5/2003 | Wittwer et al. | |
| 6,753,141 B2 | 6/2004 | Bernard et al. | |
| 6,960,437 B2 | 11/2005 | Enzelberger et al. | |
| 2001/0041357 A1 * | 11/2001 | Fouillet et al. | 435/91.1 |
| 2002/0086439 A1 * | 7/2002 | Nagle et al. | 436/180 |
| 2002/0197603 A1 * | 12/2002 | Chow | B01L 3/5027 435/6.19 |
| 2003/0008308 A1 * | 1/2003 | Enzelberger et al. | 435/6 |
| 2003/0224434 A1 | 12/2003 | Wittwer et al. | |
| 2004/0115838 A1 | 6/2004 | Quake et al. | |
| 2005/0129582 A1 * | 6/2005 | Breidford et al. | 422/100 |
| 2005/0202470 A1 | 9/2005 | Sundberg et al. | |
| 2005/0233335 A1 | 10/2005 | Wittwer et al. | |
| 2006/0019253 A1 | 1/2006 | Wittwer et al. | |
| 2008/0176289 A1 * | 7/2008 | Zeng | B01L 7/52 435/91.2 |
| 2009/0047713 A1 * | 2/2009 | Handique | B01L 3/502723 435/91.2 |

OTHER PUBLICATIONS

Merriam-Webster, defintion of "port," attached, accessed Jul. 22, 2014.*
Li et al. (A Continuous-Flow Polymerase Chain Reaction Microchip With Regional Velocity Control, J Microelectromech Syst. Feb. 1, 2006; 15(1): 223-236).*
Kopp et al. (Chemical Amplification: Continuous-Flow PCR on a Chip, Science May 15, 1998:vol. 280, Issue 5366, pp. 1046-1048).*

* cited by examiner

*Primary Examiner* — Aaron Priest
(74) *Attorney, Agent, or Firm* — Rothwell, Figg, Ernst & Manbeck, P.C.

(57) ABSTRACT

A system for amplifying nucleic acids is disclosed which, in one embodiment, includes a fluidic device having a sample channel and a heat exchange channel disposed sufficiently close to the sample channel such that a heat exchange fluid in the heat exchange channel can cause a sample in the sample channel to gain or lose heat at desired levels. In one illustrative embodiment, the system further includes three reservoirs coupled to the heat exchange channel and a temperature control system configured to heat fluids stored in the respective reservoirs at different temperatures. One or more pumps and a controller are configured to cause fluid stored in the reservoirs to enter and flow through the heat exchange channel at different times.

30 Claims, 10 Drawing Sheets

SYSTEMS AND METHODS FOR THE AMPLIFICATION OF DNA

BACKGROUND

Field of the Invention

The present invention relates to systems and methods for amplifying nucleic acids. In some embodiments, the invention relates to microfluidic PCR analysis systems using microfluidic temperature controlled channels.

Discussion of the Background

The amplification and detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. PCR is perhaps the most well-known of a number of different amplification techniques.

PCR is a powerful technique for amplifying short sections of DNA. With PCR, one can quickly produce millions of copies of DNA starting from a single template DNA molecule. PCR includes a three phase temperature cycle of denaturation of DNA into single strands, annealing of primers to the denatured strands, and extension of the primers by a thermostable DNA polymerase enzyme. This cycle is repeated so that there are enough copies to be detected and analyzed. In principle, each cycle of PCR could double the number of copies. In practice, the multiplication achieved after each cycle is always less than 2. Furthermore, as PCR cycling continues, the buildup of amplified DNA products eventually ceases as the concentrations of required reactants diminish. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

Real-time PCR refers to a growing set of techniques in which one measures the buildup of amplified DNA products as the reaction progresses, typically once per PCR cycle. Monitoring the accumulation of products over time allows one to determine the efficiency of the reaction, as well as to estimate the initial concentration of DNA template molecules. For general details concerning real-time PCR see *Real-Time PCR: An Essential Guide*, K. Edwards et al., eds., Horizon Bioscience, Norwich, U.K. (2004).

Several different real-time detection chemistries now exist to indicate the presence of amplified DNA. Most of these depend upon fluorescence indicators that change properties as a result of the PCR process. Among these detection chemistries are DNA binding dyes (such as SYBR® Green) that increase fluorescence efficiency upon binding to double stranded DNA. Other real-time detection chemistries utilize Forster resonance energy transfer (FRET), a phenomenon by which the fluorescence efficiency of a dye is strongly dependent on its proximity to another light absorbing moiety or quencher. These dyes and quenchers are typically attached to a DNA sequence-specific probe or primer. Among the FRET-based detection chemistries are hydrolysis probes and conformation probes. Hydrolysis probes (such as the TaqMan® probe) use the polymerase enzyme to cleave a reporter dye molecule from a quencher dye molecule attached to an oligonucleotide probe. Conformation probes (such as molecular beacons) utilize a dye attached to an oligonucleotide, whose fluorescence emission changes upon the conformational change of the oligonucleotide hybridizing to the target DNA.

A number of commercial instruments exist that perform real-time PCR. Examples of available instruments include the Applied Biosystems PRISM 7500, the Bio-Rad iCylcer, and the Roche Diagnostics LightCycler 2.0. The sample containers for these instruments are closed tubes which typically require at least a 10 µl volume of sample solution.

More recently, a number of high throughput approaches to performing PCR and other amplification reactions have been developed, e.g., involving amplification reactions in microfluidic devices, as well as methods for detecting and analyzing amplified nucleic acids in or on the devices. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones.

To have good yield of a target product, one has to control the sample temperature at different levels very accurately. And to reduce the process time, one has to heat up or cool down the sample to desired temperature very quickly.

One specific approach for regulating temperature within the devices is to employ external temperature control sources. Examples of such sources include, but are not limited to, heating blocks and water baths. Another option is to utilize a heating element such as a resistive heater that can be adjusted to a particular temperature. Another temperature controller includes Peltier controllers (e.g., INB Products thermoelectric module model INB-2-(11-4)1.5). This controller can be utilized to achieve effective thermal cycling or to maintain isothermal incubations at any particular temperature.

In some devices and applications, heat exchangers can also be utilized in conjunction with one of the temperature control sources to regulate temperature. Such heat exchangers typically are made from various thermally conductive materials (e.g., various metals and ceramic materials) and are designed to present a relatively large external surface area to the adjacent region. Often this is accomplished by incorporating fins, spines, ribs and other related structures into the heat exchanger. Other structures include coils and sintered structures. In certain devices, heat exchangers such as these are incorporated into a holding space, chamber or detection area.

Conventional heat exchangers that can be utilized in certain applications are discussed, for example, in U.S. Pat. No. 6,171,850 which discloses a reaction receptacle that includes a plurality of reservoirs disposed in the surface of a substrate. Additional methods of temperature control for microfluidic systems are known which include, for example: a thermal cycling system using the circulation of temperature controlled water to the underside of a microtiter plate (U.S. Pat. No. 5,508,197); a thermal cycling system using infrared heating and air cooling (U.S. Pat. No. 6,413,766); a microfluidic chip where flow travels through several static temperature zones (U.S. Pat. No. 6,960,437); the use of exothermic and endothermic materials to heat up and cool down the PCR samples (U.S. patent application publication US2005/012982).

In conventional systems temperature accuracy and thermal cycling speeds are issues to be resolved. For example, the accuracy of the temperature of any bath used to heat a microchannel and the bath's subsequent conduction of heat to the microchannel is important in that certain stages of PCR processing take place at well-defined temperatures. The thermal cycling speed refers to the time between stabilization from one temperature to another in a heating cycle. For example in the PCR process, the thermal cycling speed refers to the time to shift from 95° C. to 55° C. to 72° C. The faster the thermal cycling speeds and the more accurate the temperature stabilization, the more efficient PCR processes can be performed.

There is a need for improved systems and methods for amplifying nucleic acids and for systems and methods for microfluidic thermal control.

SUMMARY

The present invention provides improved systems and methods for amplifying nucleic acids and systems and methods for microfluidic temperature control.

A method according to some embodiments of the invention includes: causing a sample of a test solution containing PCR reagents to move through a sample channel of a fluidic device and while the sample is moving through at least a section of the sample channel: (1) for a first period of time, causing a first heat exchange fluid stored in a first container and regulated at a first temperature while stored in the first container to exit the first container and move through a heat exchange channel of the fluidic device after exiting the first container; (2) for a second period of time, causing a second heat exchange fluid stored in a second container and regulated at a second temperature while stored in the second container to exit the second container and move through the heat exchange channel after exiting the second container; and (3) for a third period of time, causing a third heat exchange fluid stored in a third container and regulated at a third temperature while stored in the third container to exit the third container and move through the heat exchange channel after exiting the third container. Steps (1)-(3) are preferably repeated at least several times. Also, it is preferred that the first period of time is different than the second period of time, which is different than the third period of time, although there may be some overlap between the time periods. It is also preferred that the first temperature is different than the second temperature, which is different than the third temperature.

In some embodiments, the method may further include causing the first heat exchange fluid to enter the third container after exiting the heat exchange channel, causing the second heat exchange fluid to enter the first container after exiting the heat exchange channel, and causing the third heat exchange fluid to enter the second container after exiting the heat exchange channel. The heat exchange fluids may be a gas, a liquid or a gas and liquid mixture. For example, the heat exchange fluids may include water and/or compressed air with pressure from 1 to 200 psia.

The heat exchange and sample channels may each have a dimension less than 2000 micrometers. For example, the heat exchange channel may have a width between about 20 and 2000 micrometers and a depth between about 20 and 2000 micrometers. The containers may have a volume of less than 2000 ml. For example, the containers may have a volume from 10 to 1000 ml.

A system according to an embodiment of the invention includes: a fluidic device comprising a sample channel and a heat exchange channel sufficiently close to the sample channel such that a heat exchange fluid in the heat exchange channel can cause a sample in the sample channel to appreciably gain or lose heat; a first reservoir having an output port coupled to an input of the heat exchange channel and having an input port coupled to an output of the heat exchange channel through a first return valve, the first reservoir storing a first heat exchange fluid; a second reservoir having an output port coupled to the input of the heat exchange channel and having an input port coupled to the output of the heat exchange channel through a second return valve, the second reservoir storing a second heat exchange fluid; a third reservoir having an output port coupled to the input of the heat exchange channel and having an input port coupled to the output of the heat exchange channel through a third return valve, the third reservoir storing a third heat exchange fluid; a temperature control system; one or more pumps; and a controller.

The temperature control system may be configured to: (a) regulate the heat exchange fluid stored in the first reservoir at a first temperature, (b) regulate the heat exchange fluid stored in the second reservoir at a second temperature, and (c) regulate the heat exchange fluid stored in the third reservoir at a third temperature.

The controller may be configured to operate the valves and the one or more pumps such that: (a) for a first period of time, the first heat exchange fluid stored in the first reservoir enters the heat exchange channel, but the second and third heat exchange fluids stored in the second and third reservoirs, respectively, do not enter the heat exchange channel; (b) for a second period of time, the second heat exchange fluid stored in the second reservoir enters the heat exchange channel, but the first and third heat exchange fluids stored in the first and third reservoirs, respectively, do not enter the heat exchange channel; and (c) for a third period of time, the third heat exchange fluid stored in the third reservoir enters the heat exchange channel, but the first and second heat exchange fluids stored in the first and second reservoirs, respectively, do not enter the heat exchange channel.

In other embodiments, a thermal exchange system for microfluidic systems includes at least one heat exchange channel, wherein the at least one heat exchange channel is configured to carry a heat exchange fluid, wherein the heat exchange channel is configured to exchange heat with a portion of a sample channel, wherein the sample channel is configured to carry a genomic sample in a buffer. The system further includes at least two reservoir tanks, a first reservoir tank and a second reservoir tank, wherein the first reservoir tank is configured to include a first heat exchange fluid at a first temperature, and the second reservoir tank is configured to include a second heat exchange fluid at a second temperature, wherein either the first or the second heat exchange fluids can be directed into the at least one heat exchange channel. In other aspects of this system, three reservoirs are included wherein the third reservoir includes a third heat exchange fluid at a third temperature.

The thermal exchange system according to one embodiment is further characterized in that the first heat exchange fluid is flowing through the at least one heat exchange channel and the portion of the sample channel is heated to about 95 degrees Celsius, the second heat exchange fluid is flowing through the at least one heat exchange channel and the portion of the sample channel is heated to about 55 degrees Celsius, and the third heat exchange fluid is flowing through the at least one heat exchange channel and the portion of the sample channel is heated to about 72 degrees Celsius.

In some embodiments, the thermal exchange system has at least one heat exchange channel that is substantially parallel to the sample channel. In other embodiments, the thermal exchange system has at least one heat exchange channel that is substantially perpendicular to the sample channel. In still other embodiments, the thermal exchange system has at least one heat exchange channel that is configured to exchange heat with substantially one side of the sample channel. In yet other embodiments, the thermal exchange system has at least one heat exchange channel that is configured to exchange heat with substantially two sides or three sides of the sample channel.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements.

DETAILED DESCRIPTION OF PREFERRED EMBODIMENTS

Figure 1:
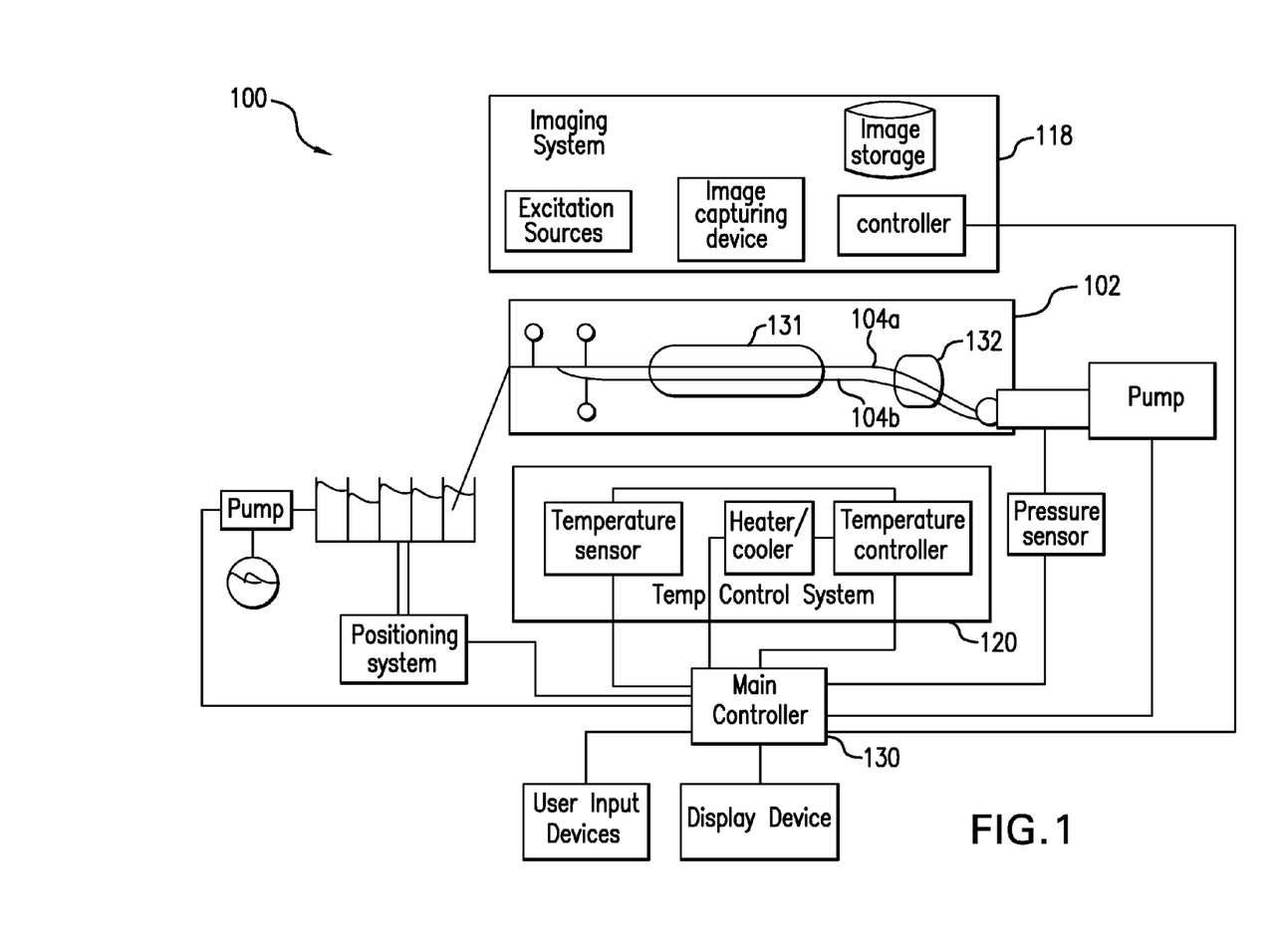
FIG. 1 is a block diagram illustrating a system according to embodiments of the invention.

FIG. 1 illustrates a functional block diagram of a system 100 for the amplification of DNA according to some embodiments of the invention. As illustrated in FIG. 1, system 100 may include a microfluidic device 102. Microfluidic device 102 may include one or more microfluidic channels 104. In the example shown, device 102 includes two microfluidic channels, channel 104a and channel 104b. Although only two channels are shown in the exemplary embodiment, it is contemplated that device 102 may have fewer than two or more than two channels. For example, in some embodiments, device 102 includes eight channels 104.

Device 102 may include two DNA processing zones, a DNA amplification zone 131 (a.k.a., PCR zone 131) and a DNA melting zone 132. A DNA sample traveling through the PCR zone 131 may undergo PCR, and a DNA sample passing through melt zone 132 may undergo high resolution thermal melting. As illustrated in FIG. 1, PCR zone 131 includes a first portion of channels 104 and melt zone 132 includes a second portion of channels 104, which is down stream from the first portion.

In order to achieve PCR for a DNA sample flowing through the PCR zone 131, the temperature of the sample must be cycled, as is well known in the art. Accordingly, in some embodiments, system 100 includes a temperature control apparatus 120. The temperature control apparatus 120 may include a temperature sensor, a heater/cooler, and a temperature controller. In some embodiments, temperature controller 120 is interfaced with main controller 130 so that main controller 130 can control the temperature of the samples flowing through the PCR zone and the melting zone.

To monitor the PCR process and the thermal melting process that occur in PCR zone 131 and melt zone 132, respectively, system 100 may include an imaging system 118. Imaging system 118 may include an excitation source, a detector, a controller, and an image storage unit.

Further features of system 100 are described in U.S. patent application Ser. No. 11/770,869, which is incorporated herein by this reference.

Figure 2A:
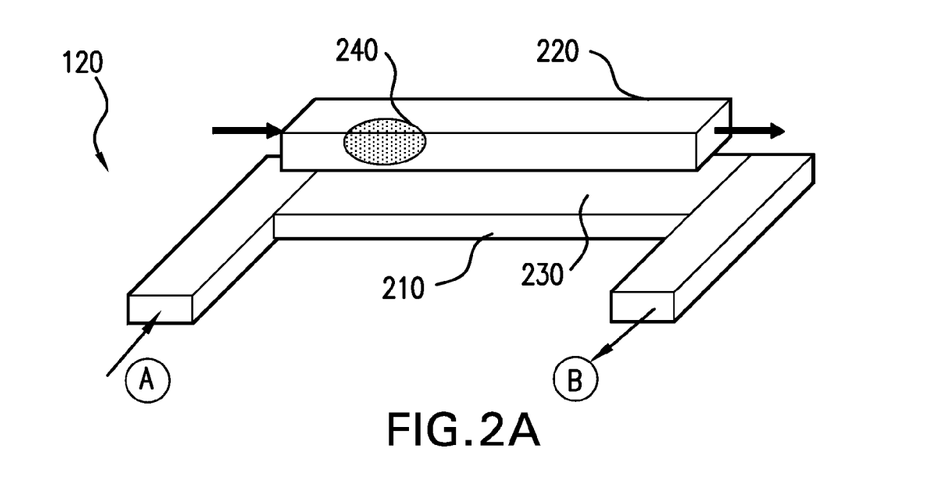
FIGS. 2A-B illustrate a temperature control system according to some embodiments of the invention.
Figure 2B:
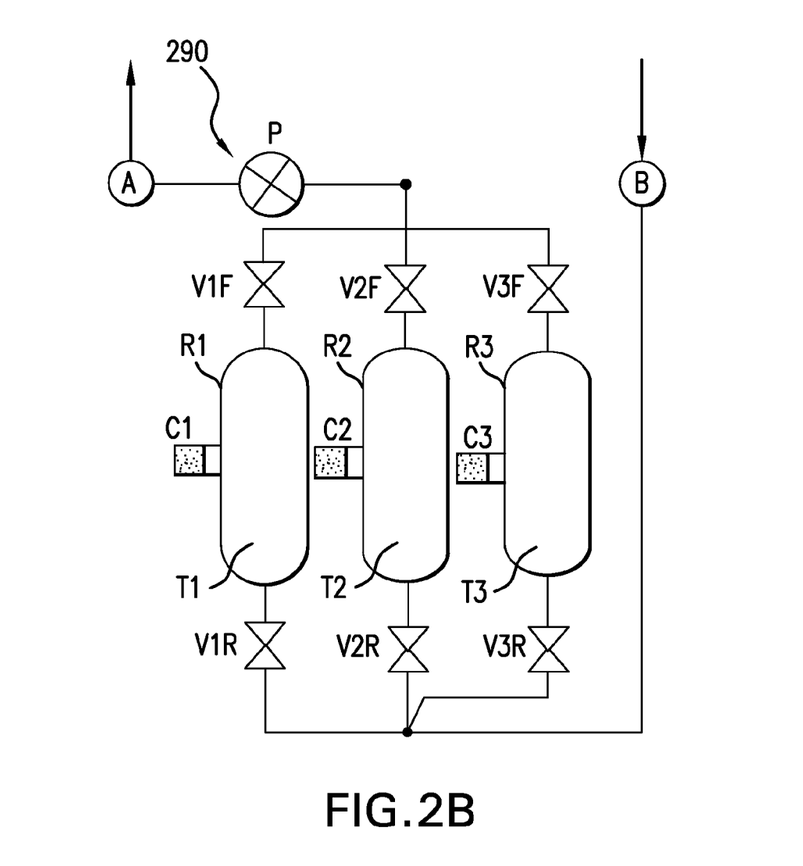

FIGS. 2A and 2B further illustrate a temperature control apparatus 120 in accordance with some embodiments of the invention. FIG. 2A illustrates a single heat exchange channel 210 and a single sample channel 104 (although, as discussed above, the invention is not limited to a single heat exchange channel 210 and/or sample channel 104). The heat exchange channel 210 is configured to carry a heat exchange fluid and configured to exchange heat with a portion 230 of a sample channel 220. The sample channel 220 can be configured to carry a bolus 240 of genomic sample material, which experiences temperature variation due to the heat exchange through the portion 230. In the one exemplary embodiment, temperature variations are performed temporally by varying the temperature of the heat exchange fluid temporally or by switching to a different heat exchange fluid at a particular time that has a different temperature.

At least one exemplary embodiment includes multiple reservoirs of various heat exchange fluids at various temperatures. For example, FIG. 2B illustrates a reservoir system for storing and directing heat exchange fluids through the heat exchange channel 210. FIG. 2B illustrates three fluid containers (a.k.a., reservoirs) T1, T2, and T3, each of which stores a fluid (e.g., a gas, a liquid or a gas and liquid mixture) and pump 290 coupled to each container for pumping fluid out of the containers and into a heat exchange channel 210 formed in chip 102. In one embodiment, the first heat exchange fluid is identical with the second heat exchange fluid, which is identical with the third heat exchange fluid, and the first heat exchange fluid comprises a gas and/or a liquid. In other embodiments, the heat exchange fluids comprise water and/or compressed air with pressure from 1 to 200 psia. In still other embodiments, the heat exchanges fluids can be different from one another. In one non-limiting example, the first heat exchange fluid is a gas, the second heat exchange fluid is a liquid and the third heat exchange fluid is gas and liquid mixture.

Each container T1-T3 includes an output port that is coupled to an input of the heat exchange channel through a forward valve. For example, the output port of T1 is coupled to the heat exchange channel through forward valve V1F, the output port of T2 is coupled to the heat exchange channel through forward valve V2F, and the output port of T3 is coupled to the heat exchange channel through forward valve V3F.

Each container T1-T3 also includes an input port that is coupled to an output of the heat exchange channel through a return valve. For example, the input port of T1 is coupled to the heat exchange channel through return valve V1R, the input port of T2 is coupled to the heat exchange channel through return valve V2R, and the input port of T3 is coupled to the heat exchange channel through return valve V3R.

As further illustrated, temperature control apparatus 120 may include a temperature control system that includes one or more temperatures controllers. For example, in the illustrated embodiment of FIG. 2B, temperature control apparatus 120 includes a temperature controller C1 for regulating the temperature of the fluid stored in T1 at a first temperature (e.g., C1 attempts to maintain the temperature of the fluid in T1 at, or close to, a predetermined temperature), a temperature controller C2 for regulating the temperature of the fluid stored in T2 at a second temperature, and a temperature controller C3 for regulating the temperature of the fluid stored in T3 at a third temperature. Each of C1, C2 and C3 may include, a sensor for sensing temperature, heating/cooling elements, and computerized controllers for controlling the heating/cooling elements based on output from a sensor.

Figure 3A:
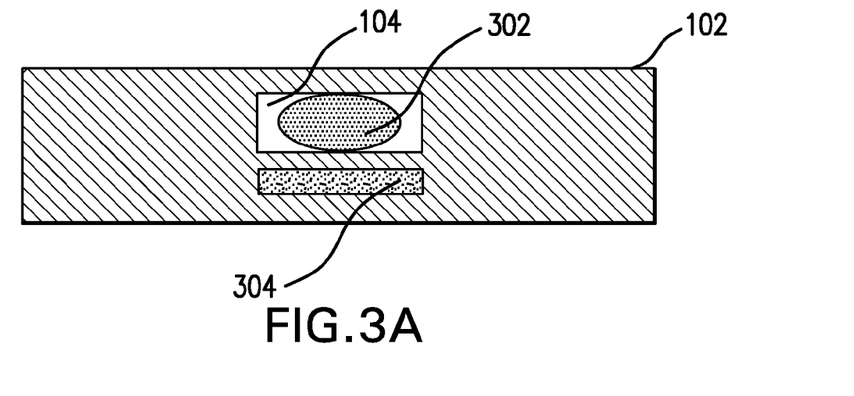
FIGS. 3A-C illustrate various configurations of a heat exchange channel according to embodiments of the invention.
Figure 3B:
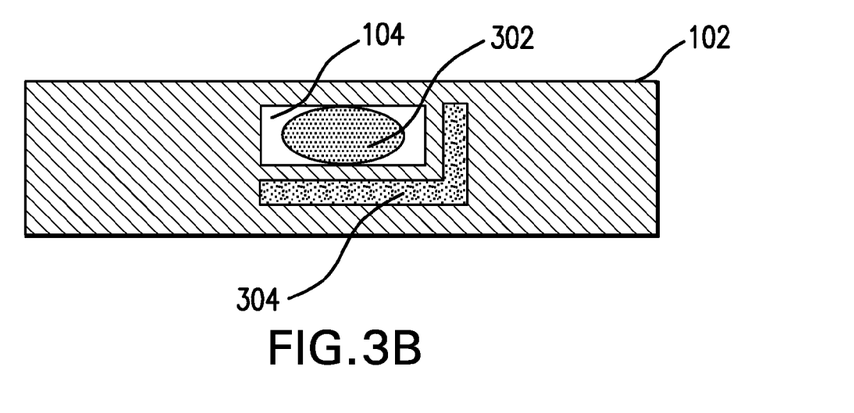
Figure 3C:
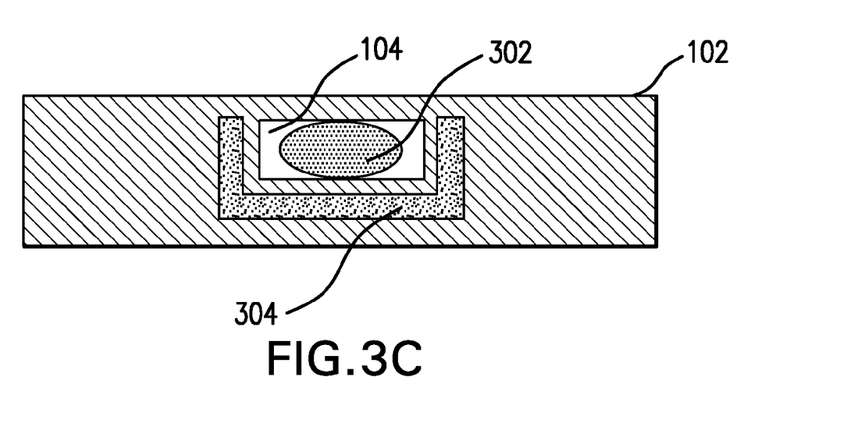

Referring now to FIGS. 3A-C, cross-sectional, end views of chip 102 are shown and serve to illustrate various different embodiments of heat exchange channel 304 and to illustrate the relationship between a sample channel 104, which carries a sample 302, and heat exchange channel 304. Sample 302 may include a solution that contains, among other things, a piece of DNA, DNA polymerase, and a primer.

As illustrated in FIGS. 3A-C, heat exchange channel 304 may only run along one side of channel 104 (see FIG. 3A), heat exchange channel 304 may be generally L shaped and run along two sides of channel 104 (see FIG. 3B), and heat exchange channel 304 may be generally U shaped and run along three side of channel 104 (see FIG. 3C). In some embodiments, channel 304 may have a width between about 10 and 3000 micrometers (more preferably between about 20 and 2000 micrometers) and a depth between about 10 and 3000 micrometers (more preferably between about 20 and 2000 micrometers).

Figure 4:
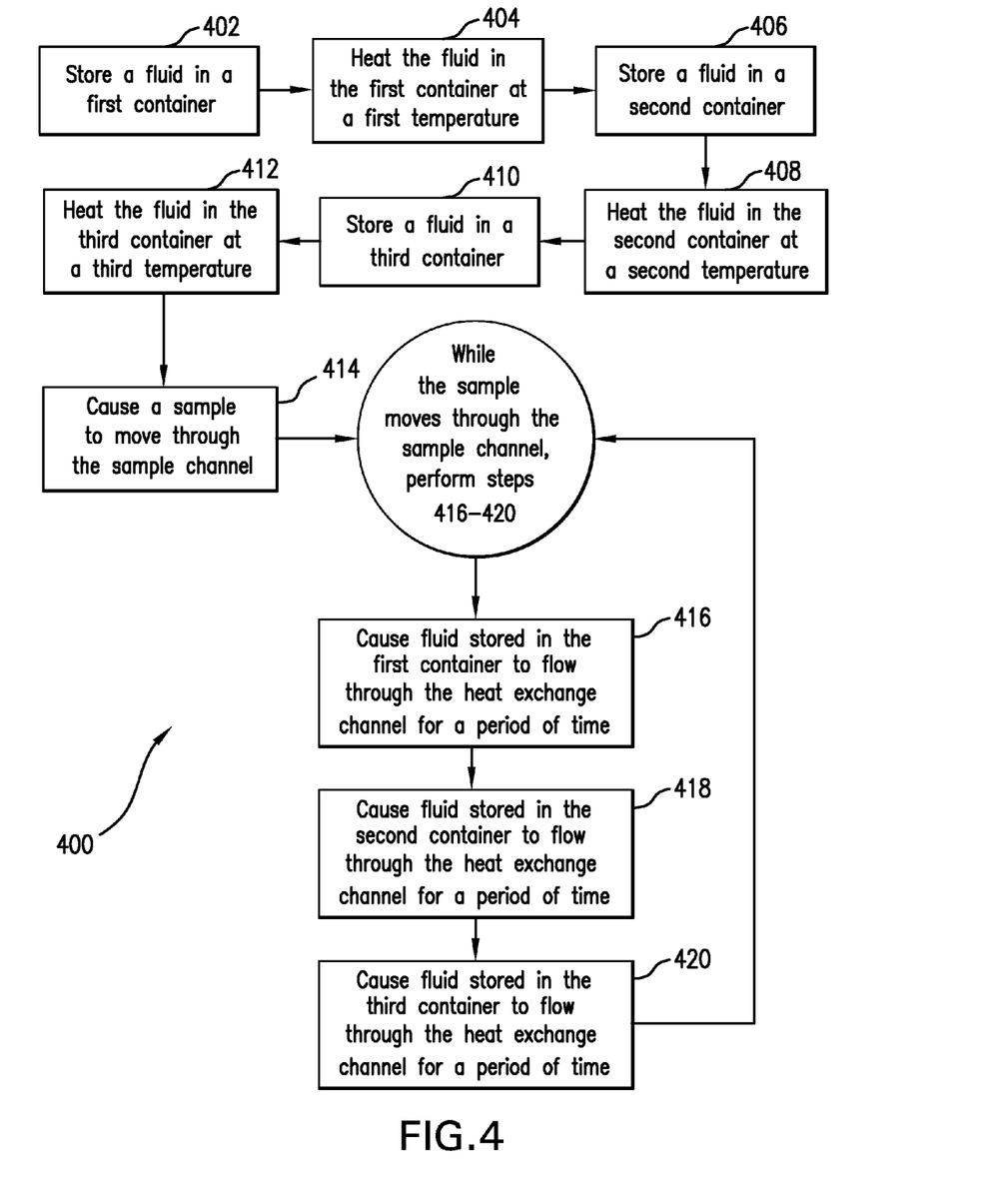
FIG. 4 illustrates a process according to some embodiments of the invention.

Referring now to FIG. 4, a flow chart illustrates a process 400 according to some embodiments of the invention. Process 400 may begin in step 402, where a fluid is stored in a first container (e.g., container T1). In step 404, the temperature of the fluid in the first container is regulated at a first temperature (e.g., at least about 80 degrees Celsius). In step 406, a fluid is stored in a second container (e.g., container T2). In step 408, the temperature of the fluid in the second container is regulated at a second temperature (e.g., a temperature not more than about 60 degrees Celsius). In step 410, a fluid is stored in a third container (e.g., container T3). In step 412, the temperature of the fluid in the third container is regulated at a third temperature (e.g., a temperature between about 60 and 80 degrees Celsius). In step 414, a sample (e.g., sample 302) is caused to flow though sample channel 104. While the sample is flowing through channel 104, steps 416-420 can be performed.

In step 416, the fluid stored in the first container is caused to flow through heat exchange channel 304 for a first amount of time. Next, in step 418, the fluid stored in the second container is caused to flow through heat exchange channel 304 for a second amount of time. Next, in step 420, the fluid stored in the third container is caused to flow through heat exchange channel 304 for a third amount of time. After step 420, steps 416-420 may be repeated a number of times. The first amount of time may be different than the second amount of time, which may be different than the third amount of time.

In one exemplary, non-limiting embodiment, the fluid stored in the first container (e.g. water) can be heated to a temperature of approximately 97 degrees Celsius so that the sample material can be heated to a temperature of approximately 95 degrees Celsius. The fluid stored in the second container (e.g. water) can be maintained at a temperature of approximately 53 degrees Celsius so that the sample material can be cooled to a temperature of approximately 55 degrees Celsius. The fluid stored in the third container (e.g. water) can be heated to a temperature of approximately 74 degrees Celsius so that the sample material can be heated to a temperature of approximately 72 degrees Celsius. Also in this exemplary embodiment, the fluid stored in the first container is caused to flow through heat exchange channel 304 for a first amount of time that can be, for example, approximately 0.3 to 2 seconds and preferably approximately 0.5 seconds. The fluid stored in the second container is caused to flow through heat exchange channel 304 for a second amount of time that can be, for example, approximately 1 to 5 seconds and preferably approximately 2 seconds. The fluid stored in the third container is caused to flow through heat exchange channel 304 for a third amount of time that can be, for example, approximately 1 to 10 seconds and preferably approximately 5 seconds. Of course, the fluid stored in the containers can be heated or cooled to different temperatures and the time periods during which the fluid flows through the heat exchange channel can be decreased or increased depending on the requirements for a given amplification reaction.

Figure 5A:
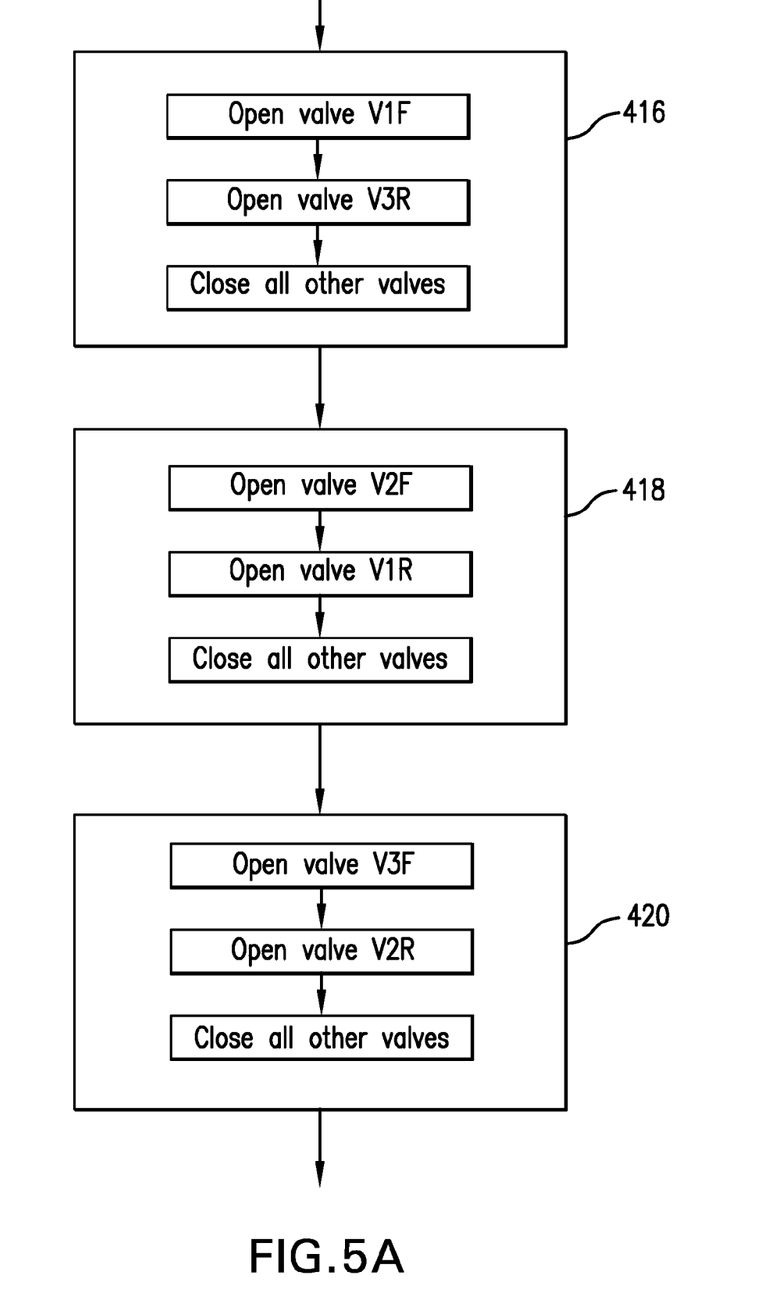
FIGS. 5A-B illustrate portions of processes according to some embodiments of the invention.

Referring now to FIG. 5A, steps 416-420 are further illustrated according to some embodiments where process 400 is implemented using the apparatus shown in FIGS. 2A-B. As shown in FIG. 5A, step 416 may include opening valve V1F, opening valve V3R and closing the other valves (V2F, V3F, V1R, and V2R), step 418 may include opening valve V2F, opening valve V1R and closing the other valves (V1F, V3F, V2R, and V3R), step 420 may include opening valve V3F, opening valve V2R and closing the other valves (V1F, V2F, V1R, and V3R). Preferably, while all the steps 416-420 are being performed, pump 290 is activated, thereby causing the fluids to flow out of a container and back into a container. The container from which the fluid flows and to which the fluid returns, of course, depends on the valves that are open at the time. For example, when step 416 is performed in accordance with the flow shown in FIG. 5A, fluid will flow out of container T1 and into container T3. Directing the fluid flow out of container T1 and into container T3, in this particular embodiment, is one exemplary way to allow more time for the fluid to reach the desired temperature level, which can increase the temperature accuracy and efficiency of the temperature cycling process.

Figure 5B:
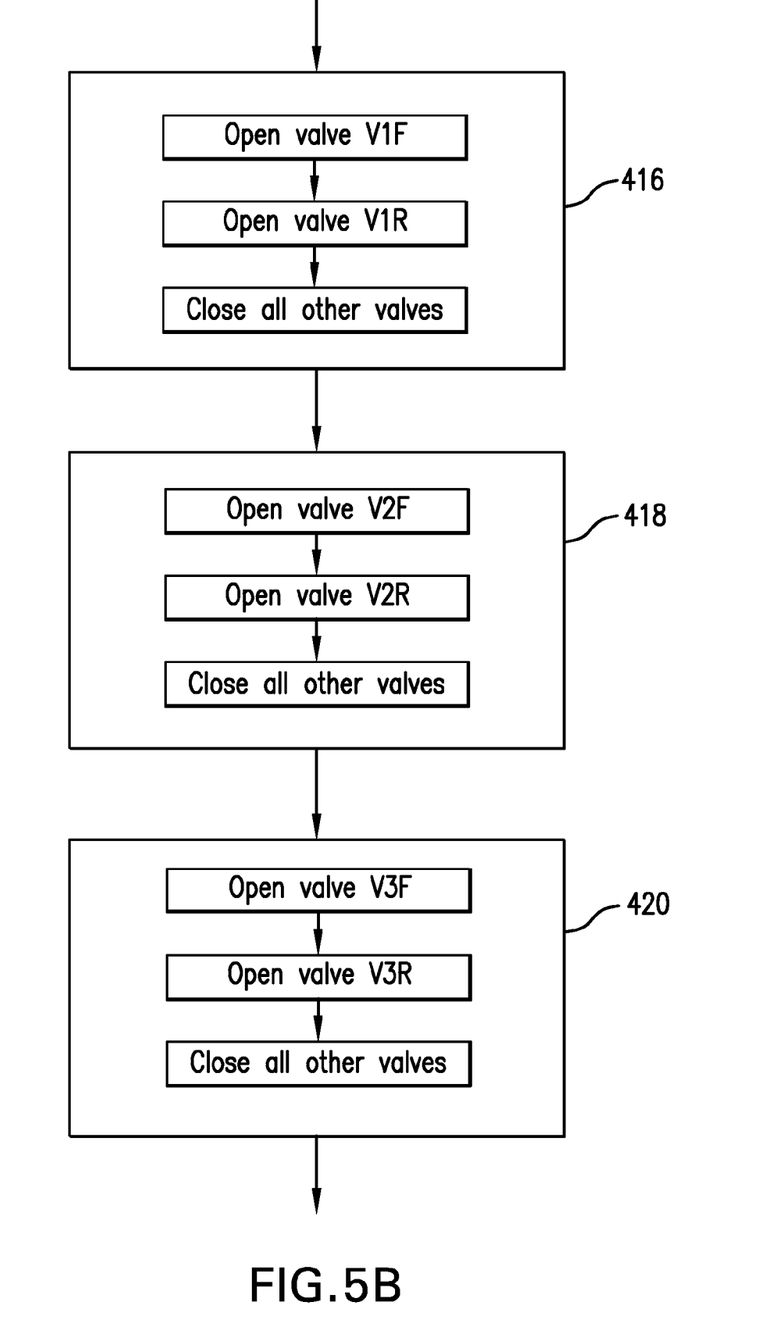

Referring now to FIG. 5B, steps 416-420 are further illustrated according to another embodiment where process 400 is implemented using the apparatus shown in FIGS. 2A-B. As shown in FIG. 5B, step 416 may include opening valve V1F, opening valve V1R and closing the other valves (V2F, V3F, V2R, and V3R), step 418 may include opening valve V2F, opening valve V2R and closing the other valves (V1F, V3F, V1R, and V3R), step 420 may include opening valve V3F, opening valve V3R and closing the other valves (V1F, V2F, V1R, and V2R). Preferably, while all the steps 416-420 are being performed, pump 290 is activated, thereby causing the fluids to flow out of a container and back into a container. In this example, when step 416 is performed in accordance with the flow shown in FIG. 5B, fluid will flow, for example, out of container T1 and back into container T1.

In another embodiment, one or more of the containers T1-T3 are constructed to have an internal bladder or baffle that separates the internal portion of the container into a first chamber and a second chamber, and wherein the first and second chambers are in fluid communication with one another by, for example, a controllable valve. In this embodiment, fluid can be controllably released from one chamber of the container (e.g. T1) through a forward valve (e.g. V1F) and can be controllably caused to flow back into the other chamber of the container through the return valve (e.g. V1R). As stated above, fluid also can controllably flow between the first chamber and the second chamber of a container through, for example, a controllable valve in the bladder or baffle separating the chambers. This embodiment may be useful, for example, in an embodiment where fluid flows out one container and back into the same container before fluid flows out of, or into, another container, as discussed in connection with the process illustrated in FIG. 5B. This embodiment also may be useful in connection with other embodiments where different fluids are used in the containers such as, for example, when a gas is used in container T1, a liquid is used in container T2 and a mixture of gas and liquid is used in container T3.

Figure 5C:
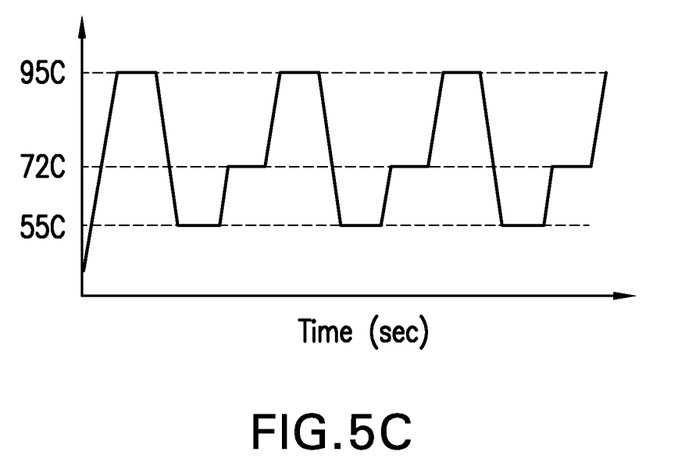
FIG. 5C illustrates a temperature profile that can result from the use of a temperature control system according to at least one exemplary embodiment.

FIG. 5C illustrates an example of a temperature versus time plot of the temperature experienced by bolus 240 as it traverses through the sample channel 220 as various heat exchange fluids flow through the heat exchange channel 210 at various times, in accordance with at least one exemplary embodiment of the present invention.

Figure 6:
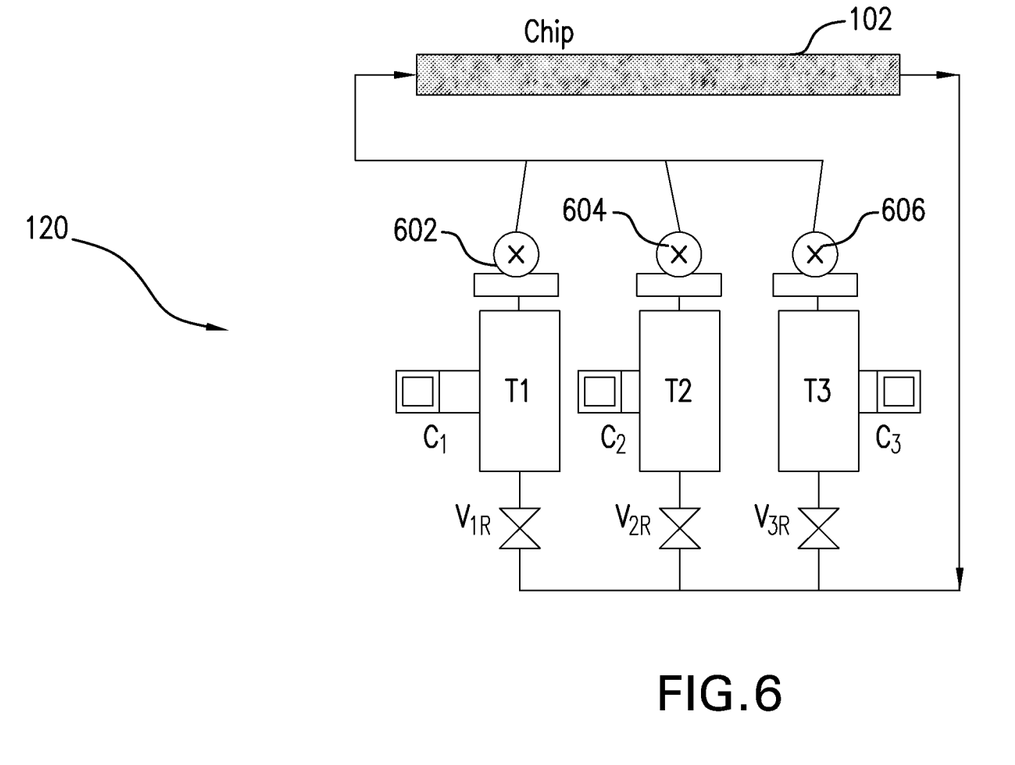
FIG. 6 illustrates a temperature control system according to other embodiments of the invention.

Referring now to FIG. 6, an apparatus 120 is illustrated according to another embodiment. The embodiment shown in FIG. 6 is similar to that shown in FIGS. 2A-B, with the exception that the forward valves V1F, V2F, and V3F are replaced with pumps 602, 604 and 606, respectively, and pump 290 is not present. The operation of the apparatus 120 in accordance with this embodiment is discussed below.

Figure 7:
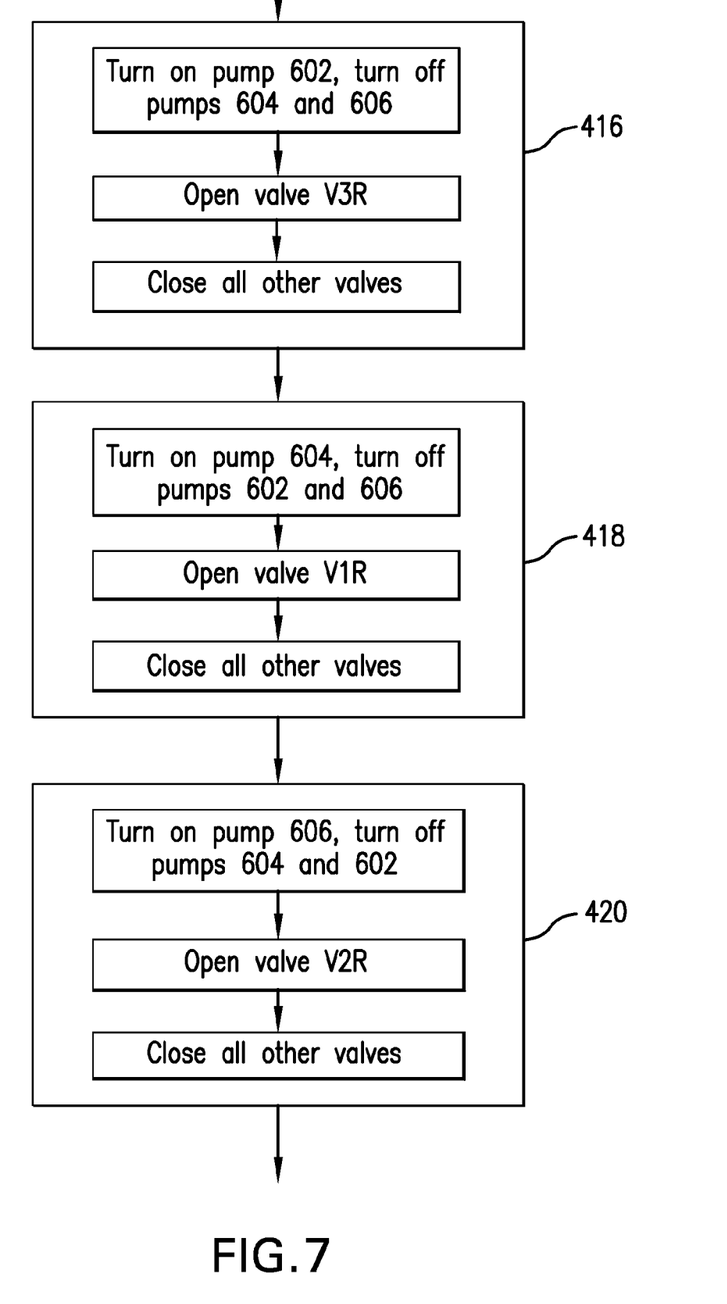
FIG. 7 illustrates a portion of a process according to some embodiments of the invention.

Referring now to FIG. 7, steps 416-420 are further illustrated according to some embodiments where process 400 is implemented using the apparatus shown in FIG. 6. As shown in FIG. 7, step 416 may include, activating only pump 602, opening valve V3R and closing the other return valves (V1R and V2R), step 418 may include activating only pump 604, opening valve V1R and closing the other return valves (V3R and V2R), step 420 may include activating only pump 606, opening valve V2R and closing the other return valves (V1R and V3R). The container from which the fluid flows and to which the fluid returns, of course, depends on the valves that are open at the time and the pump that is activated. For example, when step 418 is performed in accordance with the flow shown in FIG. 7, fluid will flow out of container T2 and into container T1. The apparatus of FIG. 6 also can be controlled such that fluid will flow out of one container and back into the same container, as discussed above.

Figure 8:
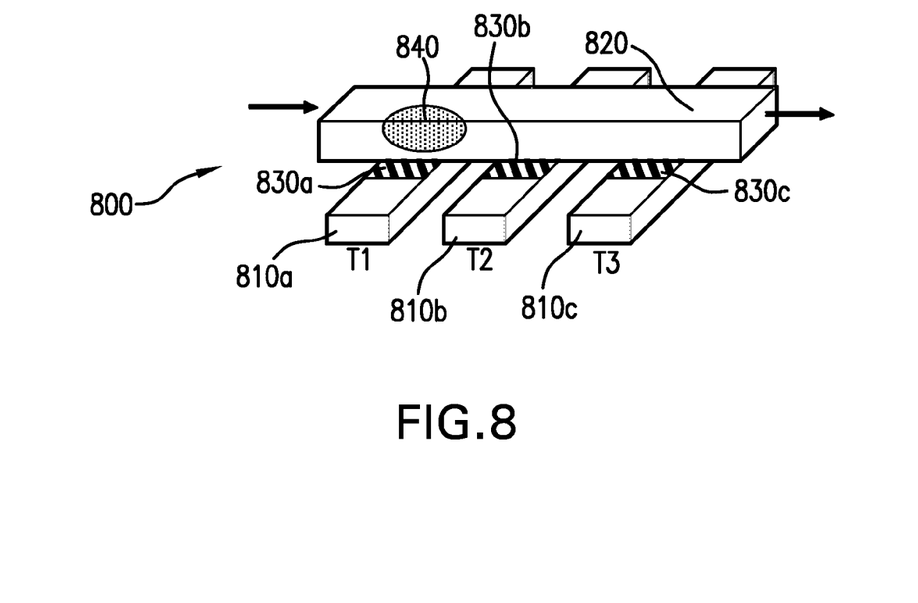
FIG. 8 illustrates a temperature control system in accordance with other embodiments of the invention.

FIG. 8 illustrates a thermal exchange system 800 in accordance with another exemplary embodiment. The thermal exchange system 800 is directed to a thermal exchange system that includes a plurality of heat exchange channels (e.g., 810a-c), each configured to carry a heat exchange fluid, where each heat exchange fluid preferably is at a different temperature. The plurality of heat exchange channels (810a-c) can be configured to lie substantially perpendicular (orthogonal) (although the invention is not limited to an orthogonal orientation) to a sample channel 820 and configured to exchange heat with a portion (e.g., 830a-c) of the sample channel. In this exemplary embodiment, a bolus 840 of genomic material traveling along the sample channel 820 experiences temperature change associated with heat exchanged in from portions of heat exchange channels 830a-c, as discussed above in connection with other embodiments.

In the embodiment of FIG. 8, heat exchange channel 810a is in fluid communication with at least container T1, heat exchange channel 810b is in fluid communication with at least container T2, and heat exchange channel 810c is in fluid communication with at least container T3. In one aspect of this embodiment, fluid is caused to flow from containers T1-T3 and through heat exchange channels 810a-c through one or more pumps and is caused to return to the containers through one or more return valves, as disclosed herein. The container from which the fluid flows and to which the fluid returns, of course, depends on the valves that are open at the time and the pump that is activated.

Figure 9:
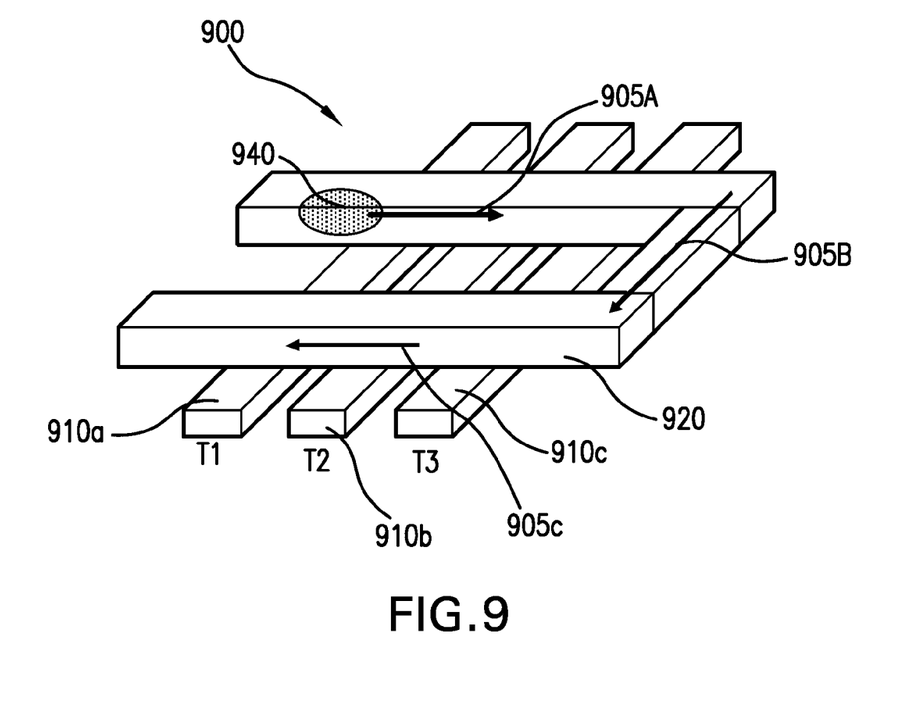
FIG. 9 illustrates a temperature control system in accordance with still other embodiments of the invention.

FIG. 9 illustrates a thermal exchange system 900 in accordance with another exemplary embodiment, which includes a curved sample channel 920, that directs a bolus 940 of genomic material back and forth (905A-C) near a plurality of heat exchange channels (910a-c), each configured to carry a heat exchange fluid, where each heat exchange fluid preferably is at a different temperature. In this exemplary embodiment, a bolus 940 of genomic material traveling along the curved sample channel 920 experiences temperature change associated with heat exchanged with portions of heat exchange channels 910a-c, as discussed above in connection with other embodiments. In this embodiment, the fluid flows from the containers T1-T3 through heat exchange channels 910a-c, for example, in the same manner described above in connection with the FIG. 8 embodiments and other embodiments described herein.

While various embodiments/variations of the present invention have been described above, it should be understood that they have been presented by way of example only, and not limitation. Thus, the breadth and scope of the present invention should not be limited by any of the above-described exemplary embodiments. Further, unless stated, none of the above embodiments are mutually exclusive. Thus, the present invention may include any combinations and/or integrations of the features of the various embodiments.

Additionally, while the processes described above and illustrated in the drawings are shown as a sequence of steps, this was done solely for the sake of illustration. Accordingly, it is contemplated that some steps may be added, some steps may be omitted, and the order of the steps may be re-arranged.

What is claimed is:
1. A system for amplifying DNA, comprising:
a microfluidic chip comprising a sample channel and a heat exchange channel formed within the microfluidic chip and sufficiently close to the sample channel such that a heat exchange fluid in the heat exchange channel can cause a sample in the sample channel to gain or lose heat at desired levels, wherein the heat exchange channel is configured to exchange heat with two sides of the sample channel;

a first reservoir having an output port coupled to an input of the heat exchange channel through a first forward valve and having an input port coupled to an output of the heat exchange channel through a first return valve, said first reservoir storing a first heat exchange fluid;

a second reservoir having an output port coupled to the input of the heat exchange channel through a second forward valve and having an input port coupled to the output of the heat exchange channel through a second return valve, said second reservoir storing a second heat exchange fluid;

a third reservoir having an output port coupled to the input of the heat exchange channel through a third forward valve and having an input port coupled to the output of the heat exchange channel through a third return valve, said third reservoir storing a third heat exchange fluid, wherein each of the first, second, and third reservoirs is divided into two chambers fluidly connected with each other by a valve, the fluid being released into the heat exchange channel from a first chamber and returned back from the heat exchange channel into the second chamber;

a temperature control system configured to: (a) regulate the heat exchange fluid stored in the first reservoir at a first temperature, (b) regulate the heat exchange fluid stored in the second reservoir at a second temperature, and (c) regulate the heat exchange fluid stored in the third reservoir at a third temperature;

one or more pumps;

an imaging system including an excitation source and an image capturing device configured to image a biological reaction within the sample channel through a sample channel region unobstructed by the heat exchange channel; and a controller configured to operate said valves and said one or more pumps such that:

(a) for a first period of time, the first heat exchange fluid stored in the first reservoir enters the heat exchange channel, but the second and third heat exchange fluids stored in the second and third reservoirs, respectively, do not enter the heat exchange channel;

(b) for a second period of time, the second heat exchange fluid stored in the second reservoir enters the heat exchange channel, but the first and third heat exchange fluids stored in the first and third reservoirs, respectively, do not enter the heat exchange channel; and (c) for a third period of time, the third heat exchange fluid stored in the third reservoir enters the heat exchange channel, but the first and second heat exchange fluids stored in the first and second reservoirs, respectively, do not enter the heat exchange channel, wherein the first period of time is different than the second period of time, which is different than the third period of time, and the first temperature is different than the second temperature, which is different than the third temperature, wherein the first heat exchange fluid is returned back to the first reservoir prior to directing the second heat exchange fluid to the heat exchange channel and the second heat exchange fluid is returned back to the second reservoir prior to directing the third heat exchange fluid to the heat exchange channel.

2. The system of claim 1, wherein the controller is further configured to operate said return valves such that the first heat exchange fluid returns to the second chamber of the third reservoir after exiting the heat exchange channel.

3. The system of claim 2, wherein the controller is further configured to operate said return valves such that the second heat exchange fluid returns to the second chamber of the first reservoir after exiting the heat exchange channel.

4. The system of claim 3, wherein the controller is further configured to operate said return valves such that the third heat exchange fluid returns to the second chamber of the second reservoir after exiting the heat exchange channel.

5. The system of claim 1, wherein the controller is further configured to operate said return valves such that the first heat exchange fluid returns to the second chamber of the first reservoir after exiting the heat exchange channel.

6. The system of claim 5, wherein the controller is further configured to operate said return valves such that the second heat exchange fluid returns to the second chamber of the second reservoir after exiting the heat exchange channel.

7. The system of claim 6, wherein the controller is further configured to operate said return valves such that the third heat exchange fluid returns to the second chamber of the third reservoir after exiting the heat exchange channel.

8. The system of claim 1, wherein the first temperature is a temperature such that when the first heat exchange fluid moves through the heat exchange channel said fluid heats a sample in the sample channel to a temperature over 80 degrees Celsius, the second temperature is a temperature such that when the second heat exchange fluid moves through the heat exchange channel said fluid cools a sample in the sample channel to a temperature under 60 degrees Celsius, and the third temperature is a temperature such that when the third heat exchange fluid moves through the heat exchange channel said fluid heats a sample in the sample channel to a temperature between 60 and 80 degrees Celsius.

9. The system of claim 1, wherein at least a portion of the heat exchange channel is beneath the sample channel and parallel with the sample channel.

10. The system of claim 1, wherein at least one dimension of the heat exchange channel and the sample channel is less than 3000 micrometers.

11. The system of claim 10, wherein the heat exchange channel has a width between about 20 and 2000 micrometers and a depth between about 20 and 2000 micrometers.

12. The system of claim 1, wherein said heat exchange fluids comprise a gas, a liquid or a gas and liquid mixture.

13. The system of claim 1, wherein said heat exchange fluids comprise water and/or compressed air with pressure from 1 to 200 psia.

14. The system of claim 12, wherein said first heat exchange fluid is different than the second heat exchange fluid, which can be the same or different than the third heat exchange fluid.

15. A system for amplifying DNA, comprising:

a microfluidic chip comprising a sample channel and a heat exchange channel formed within the microfluidic chip sufficiently close to the sample channel such that a heat exchange fluid in the heat exchange channel can cause a sample in the sample channel to gain or lose heat at desired levels, wherein the heat exchange channel is configured to exchange heat with two sides of the sample channel;

a first reservoir having an output port coupled to an input of the heat exchange channel through a first forward valve and having an input port coupled to an output of the heat exchange channel through a first return valve, said first reservoir storing a first heat exchange fluid;

a second reservoir having an output port coupled to the input of the heat exchange channel through a second forward valve and having an input port coupled to the output of the heat exchange channel through a second return valve, said second reservoir storing a second heat exchange fluid;

a third reservoir having an output port coupled to the input of the heat exchange channel through a third forward valve and having an input port coupled to the output of the heat exchange channel through a third return valve, said third reservoir storing a third heat exchange fluid, wherein each of the first, second, and third reservoirs is divided into two chambers fluidly connected with each other by a valve, the fluid being released into the heat exchange channel from a first chamber and returned back from the heat exchange channel into the second chamber;

temperature control means for: (a) regulating the heat exchange fluid stored in the first reservoir at a first temperature, (b) regulating the heat exchange fluid stored in the second reservoir at a second temperature, and (c) regulating the heat exchange fluid stored in the third reservoir at a third temperature;

an imaging system including an excitation source and an image capturing device for imaging a biological reaction within the sample channel;

pump means for pumping said heating exchange fluids out of said reservoirs; and control means for operating said return valves and said pump means such that:

(a) for a first period of time, the first heat exchange fluid stored in the first reservoir is able to enter the heat exchange channel, but the second and third heat exchange fluids stored in the second and third reservoirs, respectively, are not able to enter the heat exchange channel;

(b) for a second period of time, the second heat exchange fluid stored in the second reservoir is able to enter the heat exchange channel, but the first and third heat exchange fluids stored in the first and third reservoirs, respectively, are not able to enter the heat exchange channel; and (c) for a third period of time, the third heat exchange fluid stored in the third reservoir is able to enter the heat exchange channel, but the first and second heat exchange fluids stored in the first and second reservoirs, respectively, are not able to enter the heat exchange channel, wherein the first period of time is different than the second period of time, which is different than the third period of time, and the first temperature is different than the second temperature, which is different than the third temperature, wherein the first heat exchange fluid is returned back to the first reservoir prior to directing the second heat exchange fluid to the heat exchange channel and the second heat exchange fluid is returned back to the second reservoir prior to directing the third heat exchange fluid to the heat exchange channel.

16. A thermal exchange system for microfluidic systems comprising:

at least one heat exchange channel, wherein the at least one heat exchange channel is configured to carry a heat exchange fluid, wherein the heat exchange channel is configured to exchange heat with a portion of a sample channel, wherein the sample channel is configured to carry a genomic sample in a buffer, wherein the at least one heat exchange channel is configured to exchange heat with two sides of the sample channel; and at least two reservoir tanks, a first reservoir tank and a second reservoir tank, wherein the first reservoir tank is configured to include a first heat exchange fluid at a first temperature, and the second reservoir tank is configured to include a second heat exchange fluid at a second temperature, wherein alternatively either the first or the second heat exchange fluids can be directed into the at least one heat exchange channel, wherein a flow control system is configured to return the first heat exchange fluid back to the first reservoir tank prior to directing the second heat exchange fluid to the heat exchange channel, wherein each of the at least two reservoir tanks has an input and output port coupled to at least one heat exchange channel through two separate valves, wherein each of the first and second reservoir tanks is divided into two chambers fluidly connected with each other by a valve, the fluid being released into the heat exchange channel from a first chamber and returned back from the heat exchange channel into the second chamber;

wherein the at least one heat exchange channel and the sample channel are formed in a single microfluidic chip; and an imaging system including an excitation source and an image capturing device for imaging a biological reaction within the sample channel.

17. The thermal exchange system according to claim 16, wherein there are three reservoirs, the first and second reservoirs and a third reservoir, wherein the third reservoir includes a third heat exchange fluid at a third temperature.

18. The thermal exchange system according to claim 17, wherein when the first heat exchange fluid is flowing through the at least one heat exchange channel and the portion of the sample channel is heated to about 95 degrees Celsius.

19. The thermal exchange system according to claim 18, wherein when the second heat exchange fluid is flowing through the at least one heat exchange channel and the portion of the sample channel is heated to about 55 degrees Celsius.

20. The thermal exchange system according to claim 19, wherein when the third heat exchange fluid is flowing through the at least one heat exchange channel and the portion of the sample channel is heated to about 72 degrees Celsius.

21. The thermal exchange system according to claim 16, wherein the at least one heat exchange channel is parallel to the sample channel.

22. The thermal exchange system according to claim 16, wherein the at least one heat exchange channel is perpendicular to the sample channel.

23. The thermal exchange system according to claim 21, wherein the at least one heat exchange channel is configured to exchange heat with three sides of the sample channel.

24. The thermal exchange system according to claim 16, wherein there is a plurality of heat exchange channels each configured to carry a heat exchange fluid, wherein each heat exchange fluid is at a different temperature from each other.

25. The thermal exchange system according to claim 24, wherein the plurality of heat exchange channels are orthogonal to the sample channel.

26. The thermal exchange system according to claim 24, wherein the plurality of heat exchange channels are parallel to a plurality of sample channels.

27. The thermal exchange system according to claim 26, wherein at least one dimension of the at least one heat exchange channel and the sample channel are less than 1000 micrometers.

28. The thermal exchange system according to claim 24, wherein said sample channel curves back and forth over said plurality of heat exchange channels.

29. The thermal exchange system according to claim 1, wherein the heat exchange channel is configured to exchange heat with three sides of the sample channel.

30. The thermal exchange system according to claim 15, wherein the heat exchange channel is configured to exchange heat with three sides of the sample channel.

* * * * *